United States Patent
Schunder et al.

(10) Patent No.: US 9,122,775 B2
(45) Date of Patent: Sep. 1, 2015

(54) MEDICAL DATA ACQUISITION AND PROVISION

(75) Inventors: Mark Schunder, Dearborn, MI (US); Krishnaswamy Venkatesh Prasad, Ann Arbor, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 648 days.

(21) Appl. No.: 12/983,545

(22) Filed: Jan. 3, 2011

(65) Prior Publication Data

US 2012/0171982 A1   Jul. 5, 2012

(51) Int. Cl.
*G06F 19/00* (2011.01)
*G08B 21/04* (2006.01)
*B60W 40/08* (2012.01)

(52) U.S. Cl.
CPC .......... *G06F 19/322* (2013.01); *G08B 21/0453* (2013.01); *B60W 40/08* (2013.01); *G06F 19/3418* (2013.01); *G06F 19/3431* (2013.01)

(58) Field of Classification Search
CPC ...... A61B 5/0002; A61B 5/145; A61B 5/411; G06F 19/3418; G06F 19/3406
USPC ......... 340/539.12, 10.41, 438, 439, 575, 576, 340/945, 286.07; 700/300
See application file for complete search history.

(56) References Cited

U.S. PATENT DOCUMENTS

| | | | | |
|---|---|---|---|---|
| 3,974,350 A * | 8/1976 | Breed | | 200/61.53 |
| 5,365,516 A * | 11/1994 | Jandrell | | 370/335 |
| 5,410,739 A * | 4/1995 | Hart | | 455/66.1 |
| 5,465,079 A * | 11/1995 | Bouchard et al. | | 340/576 |
| 5,653,462 A * | 8/1997 | Breed et al. | | 280/735 |
| 5,686,910 A * | 11/1997 | Timm et al. | | 340/988 |
| 5,748,473 A * | 5/1998 | Breed et al. | | 701/45 |
| 5,829,782 A * | 11/1998 | Breed et al. | | 280/735 |
| 5,845,255 A | 12/1998 | Mayaud | | |
| 5,848,802 A * | 12/1998 | Breed et al. | | 280/735 |
| 5,901,978 A * | 5/1999 | Breed et al. | | 280/735 |
| 6,078,853 A | 6/2000 | Ebner et al. | | |
| 6,104,296 A * | 8/2000 | Yasushi et al. | | 340/576 |
| 6,128,482 A | 10/2000 | Nixon et al. | | |
| 6,272,411 B1 * | 8/2001 | Corrado et al. | | 701/45 |
| 6,282,475 B1 * | 8/2001 | Washington | | 701/49 |
| 6,330,499 B1 | 12/2001 | Chou et al. | | |
| 6,353,785 B1 * | 3/2002 | Shuman et al. | | 701/48 |
| 6,445,300 B1 * | 9/2002 | Luman | | 340/573.1 |
| 6,474,683 B1 * | 11/2002 | Breed et al. | | 280/735 |

(Continued)

OTHER PUBLICATIONS

Medical Procedures/Surgical Procedures What's the Cost?, 1st Health Insurance Quotes,com, printed Oct. 30, 2010.

(Continued)

*Primary Examiner* — Jennifer Mehmood
*Assistant Examiner* — Rufus Point
(74) *Attorney, Agent, or Firm* — Jennifer M. Stec; Brooks Kushman P.C.

(57) ABSTRACT

A computer-implemented method includes determining a user account associated with a vehicle occupant. The method also includes detecting the presence of at least one active monitoring device. The method further includes determining an association between the active monitoring device and the user account and periodically downloading device information from the active monitoring device to a vehicle computing system. Finally, the method includes storing downloaded device information in association with the user account.

16 Claims, 5 Drawing Sheets

(56) References Cited

U.S. PATENT DOCUMENTS

| | | | |
|---|---|---|---|
| 6,602,191 B2 | 8/2003 | Quy | |
| 6,603,999 B2 | 8/2003 | Servaas | |
| 6,734,799 B2* | 5/2004 | Munch | 340/576 |
| 6,762,684 B1* | 7/2004 | Camhi | 340/573.1 |
| 6,778,672 B2* | 8/2004 | Breed et al. | 381/86 |
| 6,793,242 B2* | 9/2004 | Breed et al. | 280/735 |
| 6,942,248 B2* | 9/2005 | Breed et al. | 280/735 |
| 6,944,536 B2 | 9/2005 | Singleton | |
| 6,945,860 B2 | 9/2005 | Matsui et al. | |
| 6,946,966 B2 | 9/2005 | Koenig | |
| 7,019,650 B2* | 3/2006 | Volpi et al. | 340/572.1 |
| 7,027,621 B1* | 4/2006 | Prokoski | 382/118 |
| 7,042,345 B2 | 5/2006 | Ellis | |
| 7,050,897 B2* | 5/2006 | Breed et al. | 701/46 |
| 7,164,117 B2 | 1/2007 | Breed et al. | |
| 7,266,430 B2* | 9/2007 | Basson et al. | 701/1 |
| RE39,871 E | 10/2007 | Skardon | |
| 7,301,464 B2 | 11/2007 | Coulter | |
| 7,534,206 B1 | 5/2009 | Lovitt et al. | |
| 7,670,288 B2 | 3/2010 | Sher | |
| 7,680,690 B1 | 3/2010 | Catalano | |
| 7,693,625 B2 | 4/2010 | Bauerle et al. | |
| 7,775,453 B2 | 8/2010 | Hara | |
| 7,792,701 B2* | 9/2010 | Basson et al. | 705/26.1 |
| 7,805,224 B2* | 9/2010 | Basson et al. | 701/1 |
| 8,078,334 B2* | 12/2011 | Goodrich | 700/300 |
| 8,104,814 B2 | 1/2012 | Sartin et al. | |
| 8,140,358 B1* | 3/2012 | Ling et al. | 705/4 |
| 8,149,111 B2* | 4/2012 | Monroe | 340/539.12 |
| 8,196,694 B2 | 6/2012 | Biondo et al. | |
| 8,229,758 B2* | 7/2012 | Moncrease | 705/2 |
| 8,350,722 B2 | 1/2013 | Tewari et al. | |
| 2001/0020902 A1* | 9/2001 | Tamura | 340/905 |
| 2001/0034617 A1* | 10/2001 | Kimata | 705/3 |
| 2002/0013788 A1 | 1/2002 | Pennell et al. | |
| 2002/0099424 A1 | 7/2002 | Ferek-Petric | |
| 2002/0118112 A1* | 8/2002 | Lang | 340/573.1 |
| 2002/0123833 A1* | 9/2002 | Sakurai et al. | 701/33 |
| 2003/0028792 A1 | 2/2003 | Plow et al. | |
| 2003/0043045 A1* | 3/2003 | Yasushi et al. | 340/576 |
| 2003/0064748 A1* | 4/2003 | Stulberger | 455/556 |
| 2003/0065432 A1* | 4/2003 | Shuman et al. | 701/48 |
| 2003/0191581 A1* | 10/2003 | Ukai et al. | 701/207 |
| 2003/0208409 A1 | 11/2003 | Mault | |
| 2004/0046666 A1* | 3/2004 | Yasuchi | 340/573.1 |
| 2004/0083318 A1* | 4/2004 | Shibasaki | 710/31 |
| 2004/0133082 A1* | 7/2004 | Abraham-Fuchs et al. | 600/300 |
| 2005/0125258 A1* | 6/2005 | Yellin et al. | 705/3 |
| 2005/0132024 A1* | 6/2005 | Habaguchi et al. | 709/219 |
| 2005/0171660 A1* | 8/2005 | Woolford et al. | 701/33 |
| 2005/0190062 A1 | 9/2005 | Sullivan et al. | |
| 2005/0192830 A1* | 9/2005 | Pugh et al. | 705/1 |
| 2006/0008058 A1 | 1/2006 | Dai et al. | |
| 2006/0015254 A1 | 1/2006 | Smith | |
| 2006/0022834 A1* | 2/2006 | Rosenfeld et al. | 340/573.1 |
| 2006/0059013 A1* | 3/2006 | Lowe | 705/2 |
| 2006/0161456 A1 | 7/2006 | Baker et al. | |
| 2006/0271394 A1 | 11/2006 | Kelly | |
| 2006/0290516 A1 | 12/2006 | Muehlsteff et al. | |
| 2007/0088624 A1 | 4/2007 | Vaughn et al. | |
| 2007/0233384 A1 | 10/2007 | Lee | |
| 2008/0033644 A1 | 2/2008 | Bannon | |
| 2008/0097552 A1* | 4/2008 | Dicks et al. | 607/60 |
| 2008/0097917 A1* | 4/2008 | Dicks et al. | 705/51 |
| 2008/0218376 A1* | 9/2008 | Dicks et al. | 340/870.01 |
| 2008/0249386 A1* | 10/2008 | Besterman et al. | 600/365 |
| 2008/0297336 A1* | 12/2008 | Lee | 340/439 |
| 2009/0070148 A1 | 3/2009 | Skocic | |
| 2009/0292555 A1 | 11/2009 | Brown | |
| 2010/0268051 A1 | 10/2010 | Prasad et al. | |
| 2010/0324817 A1 | 12/2010 | Hansen et al. | |
| 2011/0193707 A1 | 8/2011 | Ngo | |
| 2011/0210867 A1 | 9/2011 | Benedikt | |
| 2011/0218839 A1 | 9/2011 | Shamaiengar | |
| 2012/0112915 A1 | 5/2012 | Strumolo | |
| 2012/0166680 A1 | 6/2012 | Masoud et al. | |
| 2012/0171982 A1 | 7/2012 | Schunder et al. | |
| 2012/0173336 A1 | 7/2012 | Strumolo | |
| 2012/0182143 A1* | 7/2012 | Gaines et al. | 340/539.12 |
| 2012/0184237 A1 | 7/2012 | Gaines et al. | |
| 2012/0185265 A1 | 7/2012 | Kochhar | |

OTHER PUBLICATIONS

Ford Motor Company, "SYNC with Navigation System," Owner's Guide Supplement, SYNC System Version 1 (Jul. 2007).
Ford Motor Company, "SYNC," Owner's Guide Supplement, SYNC System Version 1 (Nov. 2007).
Ford Motor Company, "SYNC with Navigation System," Owner's Guide Supplement, SYNC System Version 2 (Oct. 2008).
Ford Motor Company, "SYNC," Owner's Guide Supplement, SYNC System Version 2 (Oct. 2008).
Ford Motor Company, "SYNC with Navigation System," Owner's Guide Supplement, SYNC System Version 3 (Jul. 2009).
Ford Motor Company, "SYNC," Owner's Guide Supplement, SYNC System Version 3 (Aug. 2009).
Kermit Whitfield, "A hitchhiker's guide to the telematics ecosystem", Automotive Design & Production, Oct. 2003, http://findarticles.com, pp. 1-3.

* cited by examiner

MEDICAL DATA ACQUISITION AND PROVISION

BACKGROUND

1. Technical Field

The illustrative embodiments generally relate to using a vehicle data system for medical data acquisition and provision.

2. Background

Keeping an accurate account of medical records and patient health data may sometimes be a difficult task. Patients may visit numerous doctors, and may often times fail to record data that they're being asked to track about themselves. Further, due to inconvenience and limitations on time, patients may fail to, or simply not realistically be able to track certain data that would otherwise be useful for diagnosis and medical assistance.

For example, if a patient has high blood pressure or a stress related condition, the patient may be asked to track blood pressure or heart rate periodically. Since many people live lives packed with numerous activities, it may become difficult or near impossible for a patient to actually monitor this data with a recommended frequency. Additionally, even if the medical data is measured, the patient may fail to accurately track all of the data. Finally, there is a possibility that the patient will forget to bring some or all of the data when reporting to a physician.

Some of the difficulties with medical record tracking are addressed by solutions such as MICROSOFT HEALTH-VAULT and GOOGLE HEALTH. These voluntary record-keeping services allow users to consolidate their medical data into one accessible source. Data from a variety of different physicians, pharmacists, dentists, optometrists, etc., can all be conglomerated in a single place.

Further, some of these services offer additional connection capabilities for medical monitoring devices. HEALTH-VAULT, for example, has the ability to store data from heart rate monitors (HRMs), blood pressure monitors (BPMs), wireless scales, etc. It may also be possible to connect other wireless devices to HEALTHVAULT.

In an environment where wireless sensors are reporting gathered information to a service such as HEALTHVAULT, those sensors typically require a local network over which they can transmit the data. While such networks may be easily available at a user's house, when a user is not in the home it may be difficult to find a network that is accessible. Further, if the user is not carrying or using a sensor at a given time, the data simply cannot be measured or taken down.

In addition to health monitoring devices, various exercise assistance and wellness devices may record data pertaining to athletic activity. This data may then be transferred, via, for example, a home wireless network, to a remote site or computer for analysis and tracking.

SUMMARY

In a first illustrative embodiment, a computer-implemented method includes determining, via a vehicle computing system (VCS), a user account associated with a vehicle occupant. The illustrative method also includes detecting, via the VCS, the presence of at least one active monitoring device. The illustrative method further includes determining, via the VCS, an association between the active monitoring device and the user account and periodically downloading device information from the active monitoring device to the VCS.

Finally, the illustrative method includes storing downloaded device information in association with the user account.

In a second illustrative embodiment, a vehicle computing apparatus (VCA) includes determining programmed logic circuitry to determine a user account associated with a wireless device present in a vehicle, the wireless device corresponding to a user for whom the user account was created. The illustrative apparatus further includes detecting programmed logic circuitry to detect the presence of at least one active monitoring device.

Also, this illustrative apparatus includes determining programmed logic circuitry to determine an association between the active monitoring device and the user account and downloading programmed logic circuitry to periodically download device information from the active monitoring device to the VCA.

This illustrative apparatus also includes storing programmed logic circuitry to store downloaded device information in association with the user account and accessing programmed logic circuitry to access a remote user medical profile to download user medical information.

The illustrative apparatus further includes updating programmed logic circuitry to update the user account with the downloaded user medical information. Finally, the illustrative apparatus includes uploading programmed logic circuitry to upload downloaded device information to the remote user medical profile.

In a third illustrative embodiment, a computer readable storage medium, storing instructions that, when executed, causes a vehicle computing system to perform the method including determining a user account associated with a wireless device present in a vehicle, the wireless device corresponding to a user for whom the user account was created. The vehicle computing system is also caused to perform the steps of detecting the presence of at least one active monitoring device and determining an association between the active monitoring device and the user account.

The illustrative embodiment is further caused to perform the steps of periodically downloading device information from the active monitoring device to the VCA and storing downloaded device information in association with the user account.

The illustrative embodiment is also caused to perform the steps of accessing a remote user medical profile to download user medical information and updating the user account with the downloaded user medical information.

Finally, the illustrative embodiment is caused to perform the step of uploading downloaded device information to the remote user medical profile.

DETAILED DESCRIPTION

Although the following describes the invention in terms of illustrative embodiments, these examples are provided for non-limiting illustrative purposes only, and are not intended to limit the scope of the invention thereto.

Figure 1:
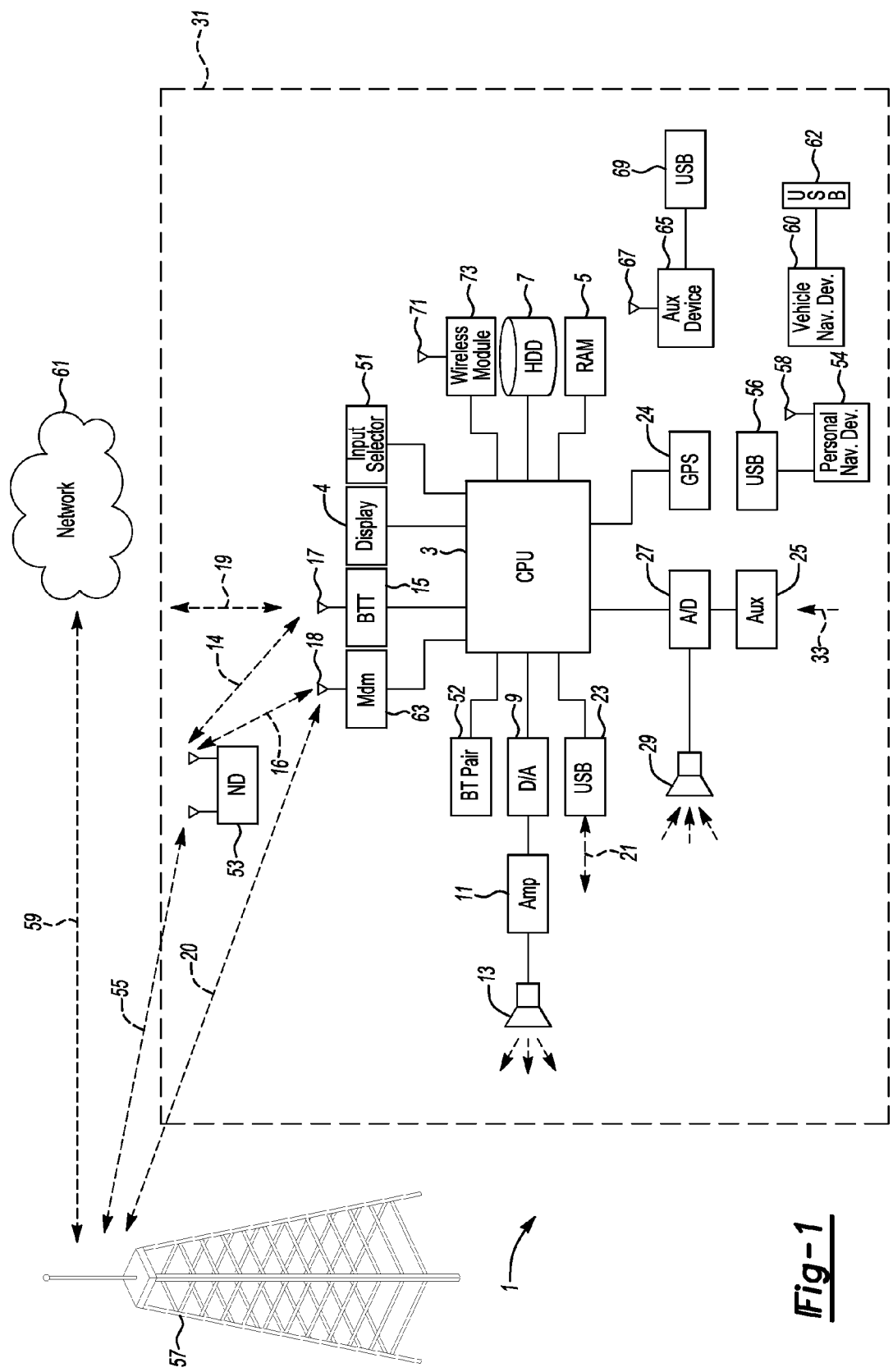
FIG. 1 shows an illustrative example of a vehicle computing system and a remote network.

FIG. 1 illustrates an example block topology for a vehicle based computing system 1 (VCS) for a vehicle 31. An example of such a vehicle-based computing system 1 is the SYNC system manufactured by THE FORD MOTOR COMPANY. A vehicle enabled with a vehicle-based computing system may contain a visual front end interface 4 located in the vehicle. The user may also be able to interact with the interface if it is provided, for example, with a touch sensitive screen. In another illustrative embodiment, the interaction occurs through, button presses, audible speech and speech synthesis.

In the illustrative embodiment 1 shown in FIG. 1, a processor 3 controls at least some portion of the operation of the vehicle-based computing system. Provided within the vehicle, the processor allows onboard processing of commands and routines. Further, the processor is connected to both non-persistent 5 and persistent storage 7. In this illustrative embodiment, the non-persistent storage is random access memory (RAM) and the persistent storage is a hard disk drive (HDD) or flash memory.

The processor is also provided with a number of different inputs allowing the user to interface with the processor. In this illustrative embodiment, a microphone 29, an auxiliary input 25 (for input 33), a USB input 23, a GPS input 24 and a BLUETOOTH input 15 are all provided. An input selector 51 is also provided, to allow a user to swap between various inputs. Input to both the microphone and the auxiliary connector is converted from analog to digital by a converter 27 before being passed to the processor. Although not shown, numerous of the vehicle components and auxiliary components in communication with the VCS may use a vehicle network (such as, but not limited to, a CAN bus) to pass data to and from the VCS (or components thereof).

Outputs to the system can include, but are not limited to, a visual display 4 and a speaker 13 or stereo system output. The speaker is connected to an amplifier 11 and receives its signal from the processor 3 through a digital-to-analog converter 9. Output can also be made to a remote BLUETOOTH device such as PND 54 or a USB device such as vehicle navigation device 60 along the bi-directional data streams shown at 19 and 21 respectively.

In one illustrative embodiment, the system 1 uses the BLUETOOTH transceiver 15 to communicate 17 with a user's nomadic device 53 (e.g., cell phone, smart phone, PDA, medical device, wellness device or any other device having wireless remote network connectivity). The nomadic device can then be used to communicate 59 with a network 61 outside the vehicle 31 through, for example, communication 55 with a cellular tower 57. In some embodiments, tower 57 may be a WiFi access point.

Exemplary communication between the nomadic device and the BLUETOOTH transceiver is represented by signal 14.

Pairing a nomadic device 53 and the BLUETOOTH transceiver 15 can be instructed through a button 52 or similar input. Accordingly, the CPU is instructed that the onboard BLUETOOTH transceiver will be paired with a BLUETOOTH transceiver in a nomadic device.

Data may be communicated between CPU 3 and network 61 utilizing, for example, a data-plan, data over voice, or DTMF tones associated with nomadic device 53. Alternatively, it may be desirable to include an onboard modem 63 having antenna 18 in order to communicate 16 data between CPU 3 and network 61 over the voice band. The nomadic device 53 can then be used to communicate 59 with a network 61 outside the vehicle 31 through, for example, communication 55 with a cellular tower 57. In some embodiments, the modem 63 may establish communication 20 with the tower 57 for communicating with network 61. As a non-limiting example, modem 63 may be a USB cellular modem and communication 20 may be cellular communication.

In one illustrative embodiment, the processor is provided with an operating system including an API to communicate with modem application software. The modem application software may access an embedded module or firmware on the BLUETOOTH transceiver to complete wireless communication with a remote BLUETOOTH transceiver (such as that found in a nomadic device).

In another embodiment, nomadic device 53 includes a modem for voice band or broadband data communication. In the data-over-voice embodiment, a technique known as frequency division multiplexing may be implemented when the owner of the nomadic device can talk over the device while data is being transferred. At other times, when the owner is not using the device, the data transfer can use the whole bandwidth (300 Hz to 3.4 kHz in one example).

If the user has a data-plan associated with the nomadic device, it is possible that the data-plan allows for broad-band transmission and the system could use a much wider bandwidth (speeding up data transfer). In still another embodiment, nomadic device 53 is replaced with a cellular communication device (not shown) that is installed to vehicle 31. In yet another embodiment, the ND 53 may be a wireless local area network (LAN) device capable of communication over, for example (and without limitation), an 802.11g network (i.e., WiFi) or a WiMax network.

In one embodiment, incoming data can be passed through the nomadic device via a data-over-voice or data-plan, through the onboard BLUETOOTH transceiver and into the vehicle's internal processor 3. In the case of certain temporary data, for example, the data can be stored on the HDD or other storage media 7 until such time as the data is no longer needed.

Additional sources that may interface with the vehicle include a personal navigation device 54, having, for example, a USB connection 56 and/or an antenna 58; or a vehicle navigation device 60, having a USB 62 or other connection, an onboard GPS device 24, or remote navigation system (not shown) having connectivity to network 61.

Further, the CPU could be in communication with a variety of other auxiliary devices 65. These devices can be connected through a wireless 67 or wired 69 connection. Also, or alternatively, the CPU could be connected to a vehicle based wireless router 73, using for example a WiFi 71 transceiver. This could allow the CPU to connect to remote networks in range of the local router 73. Auxiliary device 65 may include, but are not limited to, personal media players, wireless health devices, portable computers, and the like.

Wireless technology is perpetually becoming a cheaper and more realistic solution for transferring information from numerous point sources to other receiving sources. A whole variety of devices are equipped with BLUETOOTH or other wireless technology, and these wireless connections can be used to send communication between the equipped devices and other devices also equipped with BLUETOOTH or other wireless communication.

One common source for wireless transceivers (or wired connections) is personal medical devices. These devices can monitor a variety of medical information, including, but not limited to, blood pressure, heart rate, blood sugar, etc. When in the presence of a connected network, these devices can be used to relay data to a storage device.

In addition to medical monitoring devices, other "health related" devices include so-called wellness devices. These devices include, but are not limited to—pedometers, exercise related heart rate monitors and personal fitness devices, GPS and mph monitors for exercise, etc. These devices may have wireless connectivity, but typically they are connected in a wired manner to a PC for analysis and uploading of data.

In the illustrative embodiments, data from these and other health-related devices can be wirelessly transferred to a vehicle computing system, either for local storage, remote uploading or both. Additionally, this information can be further transferred to a secondary wireless device, such as a cellular phone, for easy access and analysis.

Additionally or alternatively, this data could be analyzed by the vehicle computing system and be used to augment the driving experience. For example, increased blood pressure or heart rate could result in a warning, or even in a suggestion of soothing music or decreased aggressiveness in driving tactics. In another illustrative example, the user could be given a suggested route with less traffic, which could presumably lead to a less aggravated driver-state.

In at least one illustrative embodiment, the vehicle itself is provided with one or more medical monitoring devices. This could include, but are not limited to, a heart rate monitor, in, for example, the steering wheel or a seat body. As another example, a seat scale could track weight, measure weight, and/or report changes in weight for a given driver/passenger.

Stored data may be added to and/or augmented by remotely stored data. For example, certain companies, such as MICROSOFT and GOOGLE offer medical data compilation services. These data stores can hold an aggregate of patient information, such as doctor reports, current drug prescriptions, etc. An account owner may be able to give the vehicle the "right" to access this data. The data could be downloaded, accessed in the vehicle, added to by stored and recorded vehicle data, analyzed for potential drug interactions, used to find preferred providers, etc.

For example, without limitation, a patient could be instructed to wear a remote blood pressure monitor (BPM) and to track their health rate. While driving, a BPM or heart rate monitor (HRM) could detect a potentially dangerous condition. Based on data available from a remote health-data site, the vehicle computing system could access preferred parameters for that specific patient, and compare those parameters against the data being tracked. If a warning condition or an emergency condition is detected, the vehicle could notify the patient of a potentially imminent problem. In addition, contact information, such as that of a care provider, could be pulled from the remote site and provided in conjunction with the warning.

Using the contact information, the vehicle computing system could give the patient the option to directly dial the physician. If the physician is unavailable, other medical contact information could be provided for use.

The system could also provide potential drug-interaction information to the patient. For example, if the above patient were unable to reach a physician, but was inclined to take Aspirin as a possible preventative measure to stave off a potential heart attack, the patient could input TYLENOL (for example) into an "intended ingestion" field and the system could inform the patient, based on data from the remote medical information provider, whether or not any potential interaction exists. The patient could then determine if any risk was worth assuming, given the seriousness of the reported condition.

If the condition worsened, the system could even call 911 on the patient's behalf, or provide an easily accessible option to quickly dial 911 (such as a large display) in the event that there was a sudden escalation in condition. If the condition was not as severe, a patient may still appreciate a warning that heart rate or blood pressure was rising, so that preventative steps could be taken.

Figure 2:
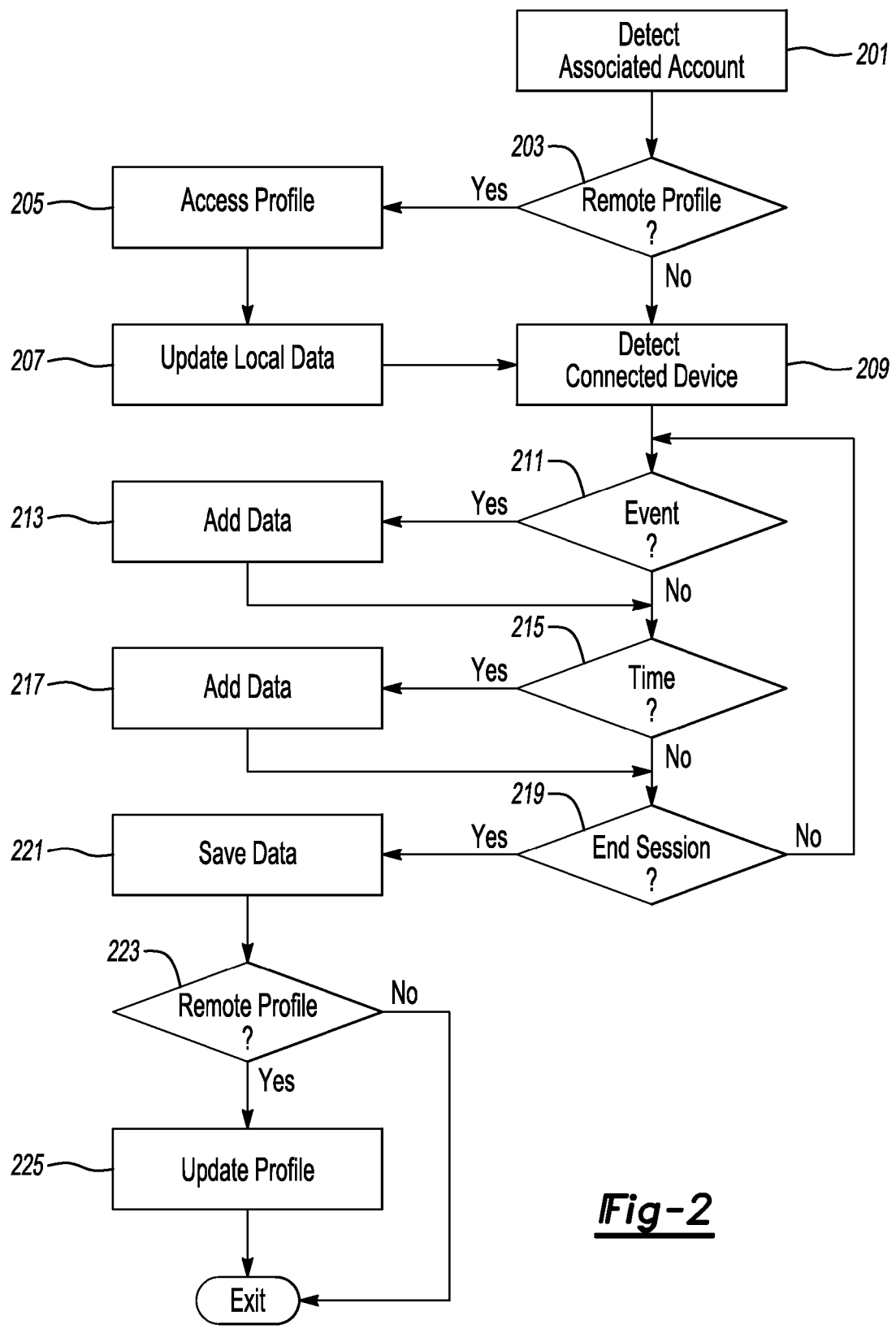
FIG. 2 shows an illustrative example of a process for storing medical data and updating a remote profile.

FIG. 2 shows an illustrative example of a process for storing medical data and updating a remote profile. In this illustrative embodiment, a vehicle computing system first establishes communication with a wireless device. Based on the connection to the device, an associated user account is identified 201.

For example, a personal HRM or BPM may transmit an identifier associated therewith. Once this device has been correlated with a user account, the vehicle may "assume" that the corresponding account owner is present as a passenger if the device is present. Additionally or alternatively, the system may ask which account the device is to be correlated to whenever the device is detected.

In another illustrative example, the presence of a cellular or other wireless device associated with the user's account, along with the presence of the previously associated medical device, may be sufficient to indicate the presence of a particular passenger. Again, the vehicle computing system may query the passengers as to the intended storage location for the data.

In still a further illustrative embodiment, a medical monitoring device, such as an HRM, may be present in the vehicle. When the device is activated, the driver may be queried for an associated account to which data is to be stored (or if data is to be stored at all).

Once the existence of a user account is established 201, the vehicle computing system checks for the presence of an existing remote profile 203 (saved on an associated website, such as, but not limited to, GOOGLE HEALTH or MICROSOFT HEALTHVAULT). If no profile exists, the system checks for the existence of one or more medical devices 209 (assuming such devices are not already connected to the system).

If the user has a remote medical and/or wellness profile associated therewith, the vehicle computing system accesses the remote site where that profile is stored 205 and updates a local data store 207. In this embodiment, this update puts the remote data in a local store for easy access in the event it is needed. A redundant copy of the data is thus stored locally too, which may be useful for backup purposes. In at least one illustrative embodiment, the remote data is not accessed and/or downloaded by the vehicle computing system, or is not accessed and/or downloaded unless it is needed. The system then proceeds to detect medical devices.

Although the example above provides for the identification of a single account and associated devices, it is also possible for multiple devices associated with multiple accounts to be accessed, monitored, have the data recorded therefrom, etc.

In this illustrative embodiment, the system periodically (or continually) checks for monitoring events 211 and time intervals 213.

In this embodiment, two different instances result in the recordation and/or analysis of data 213, 217). If an event occurs (high blood pressure, irregular heart rate, arrival at the vehicle after completion of exercise, etc.), the data from that event is recorded 213, analyzed 213, and any required action, such as a warning or notification, may also occur.

Additionally or alternatively, every periodic interval 215 data is similarly recorded and analyzed 217.

In addition for checking to data recordation points, the vehicle computing system also checks to see if a recordation session has ended 219. If the session has not ended, the system continues to check for recordation points. Once the session ends (device disabled, key off, vehicle put in park, etc.), the vehicle computing system saves the data 221. This save could be to a local and/or a remote storage location.

After storing the data (or instead of storing the data), the illustrative process determines if a remote profile is associated with the user account. For example, a MICROSOFT HEALTHVAULT or a GOOGLE HEALTH or similar account. If there is a profile associated with the account that needs updating, the vehicle computing system updates a user profile 225 and then exits. If there is no associated account that needs updating, the system simply exits.

Figure 3:
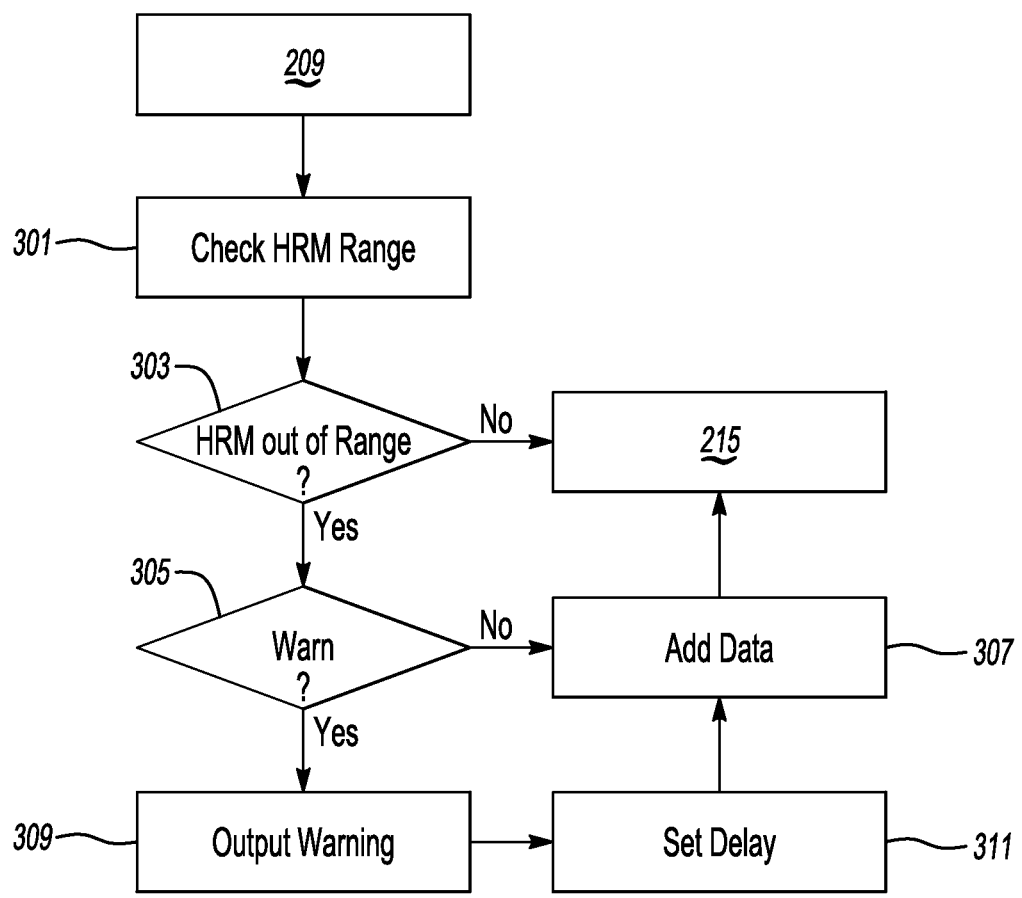
FIG. 3 shows an illustrative example of a process for warning a patient of a dangerous condition.

FIG. 3 shows an illustrative example of a process for warning a patient of a dangerous condition. In this illustrative example, this process corresponds to an "event" 211 in FIG. 2, but it could be an independent or different consideration as well.

In this exemplary embodiment, the vehicle computing system checks a preset range for a device 301 (BPM, HRM, blood glucose monitor (BGM), etc.). This range could be determined by an associated medical profile, or it could be a generically recommended medical range for all people, for a given weight/height, etc.

If the device reads outside the range 303 (i.e., in a warning or event condition), the system checks to see if a warning should be delivered 305. If the device remains within range, the system continues processing at step 215 in this embodiment.

If a warning is requested, the system proceeds to play the warning 309 and then, in this illustrative embodiment, sets a delay 311 (so as to not repeat the warning again immediately upon the next "event check"). Of course, the delay could be foregone if desired.

Warnings may be automatically set by the system, or may be requested by a user. In instances where warnings are not needed, it could be due to a device reading not triggering a warning, or a warning "off" state, or other suitable condition.

Figure 4:
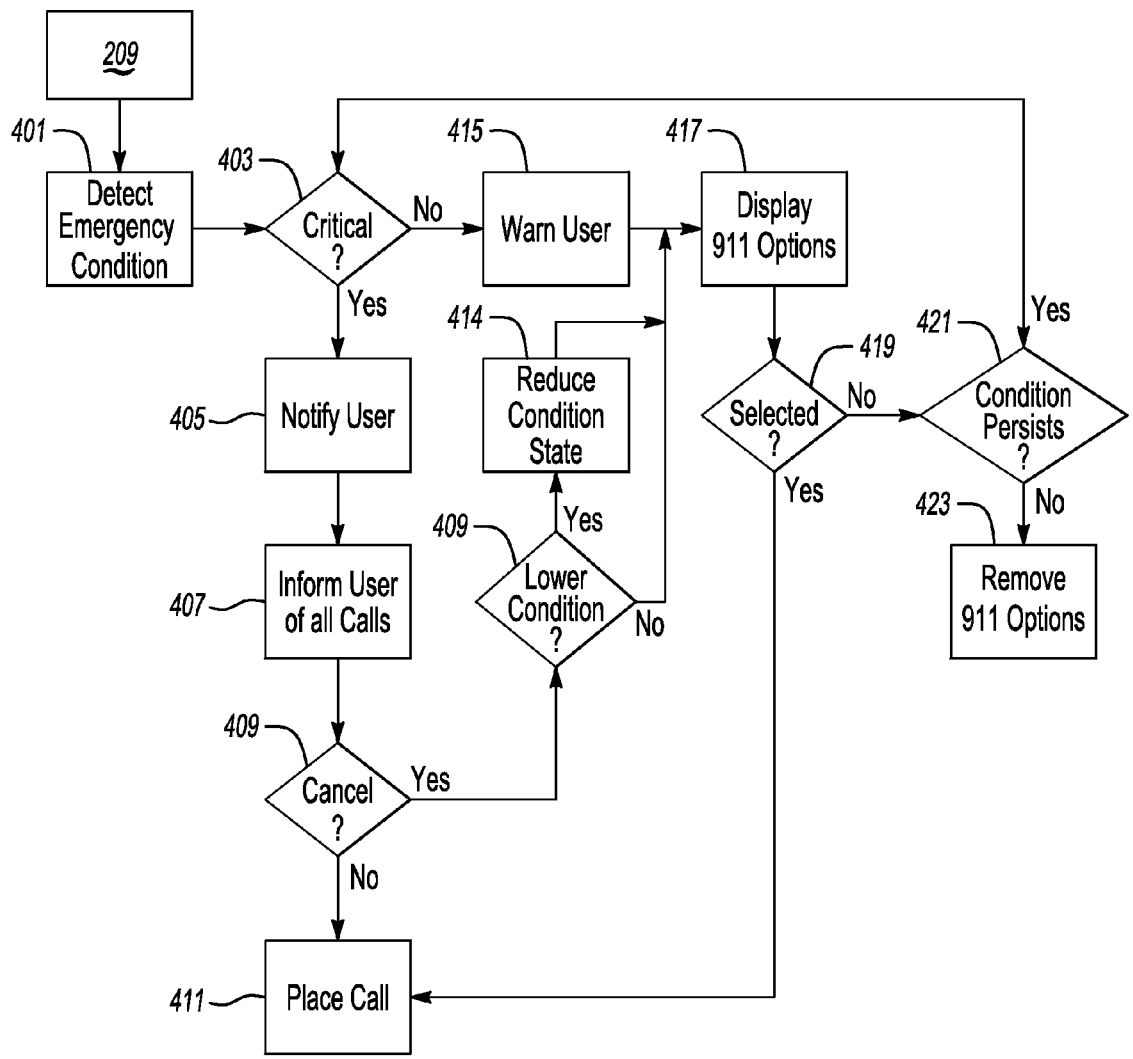
FIG. 4 shows an illustrative example of warning a patient of an emergency condition.

FIG. 4 shows an illustrative example of warning a patient of an emergency condition. In this illustrative embodiment, the vehicle computing system detects an emergency condition 401. Although this step follows step 209 in this exemplary process, this process could also be a stand-alone emergency process provided for any medical device or detection system capable of detecting a critical medical condition in a vehicle occupant.

Again, the emergency medical condition could be dictated by predefined parameters for a particular user, defined by generalized parameters, or defined by a combination of both.

In this embodiment, the system first determines if the condition is critical 403 (it may also be possible to err on the side of caution and assume all conditions qualifying as emergency conditions are critical, although in this illustrative embodiment a distinction is made between critical and emergency conditions).

If the condition is not critical, the system provides a verbal or visual (if possible) warning to a user 415, and displays or otherwise provides an easy-access 911 option 417.

For example, in a vehicle environment where a navigation or other touch-screen display is available, the vehicle computing system may provide a large or prominently displayed 911 option. This option could be immediately selected and place a call 411, if an emergency condition escalates. Similarly, if a display is not available, the system could report an audible option, such as "quick 911 is now enabled, speak 911 to immediately place an emergency call."

If the 911 option is not selected (or activated), the system checks to see if the emergency condition persists 421. If the condition has expired, the system removes the option so that 911 will not accidentally be contacted 423. If the condition persists, however, the check for criticality is again made 403 in case a previously emergency non-critical condition has escalated to a critical condition.

If the condition is ever detected as being a critical one, in this embodiment, the system notifies the user of the detected critical condition 405. In this embodiment, a critical condition includes conditions that may present an immediate driving hazard. Additionally, the critical condition may render the driver unable to respond, so in this embodiment, the system also prepares to place a 911 call.

Emergency call systems may require that a user be given the option to cancel a call being otherwise automatically placed, so in this embodiment, the system informs the user that a 911 call is about to be placed. If the user does not elect to cancel the call 409, the 911 call is placed 411. In this embodiment, if the user is rendered unconscious, comatose, or otherwise in a state where the user cannot respond, the system will automatically place the call, because the user will be unable to cancel the call (assuming someone else in the vehicle does not cancel the call).

Even if the call is canceled by the user or by another passenger, the system may still provide a "quick 911" option 417. For example, the system may check to see if the condition status should be lowered 413. This could be based on another user inquiry or a level of criticality. Lowering the condition state may prevent repeated unnecessary attempts to call 911 automatically.

If the condition status is acceptable for lowering, the state is reduced from critical to emergency 414 and, in either event, the "quick 911" option is still displayed 417 (at least in this embodiment).

Figure 5:
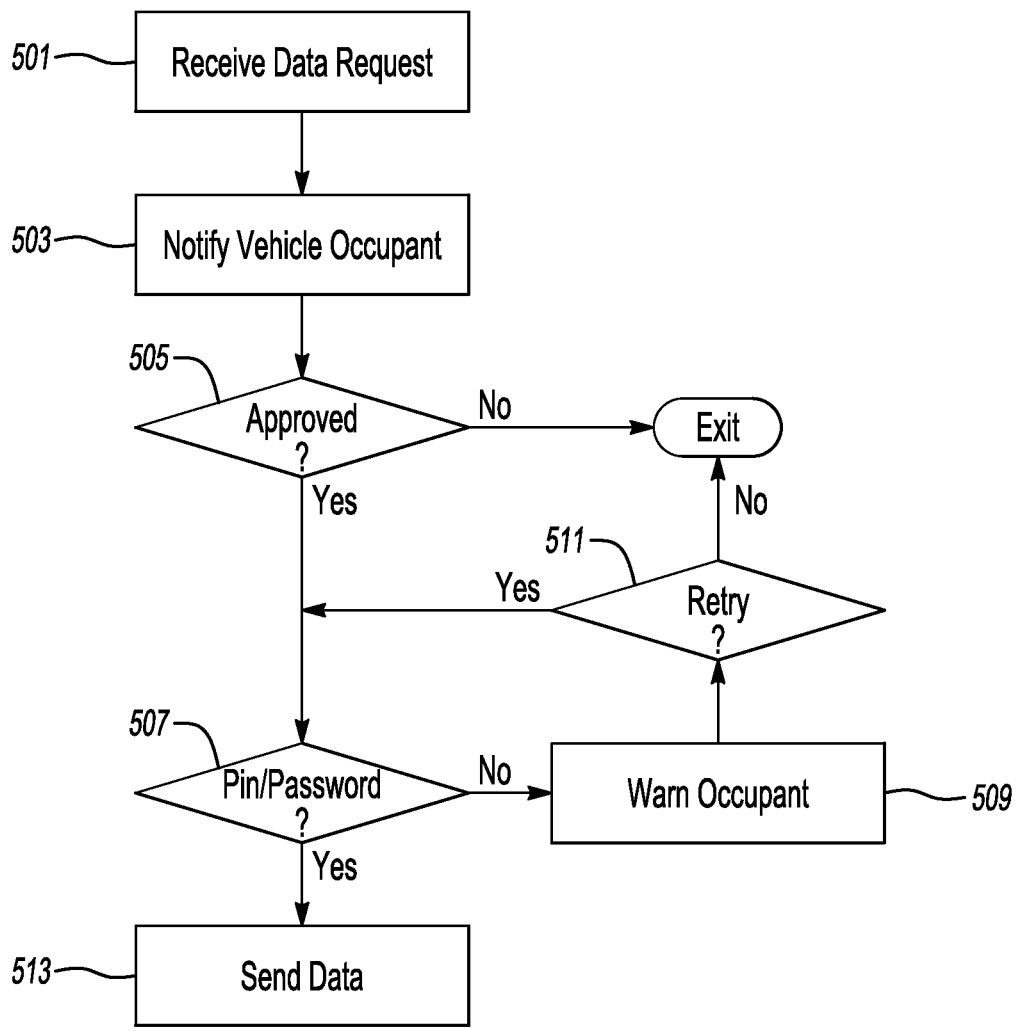
FIG. 5 shows an illustrative example of a data transfer request process.

FIG. 5 shows an illustrative example of a data transfer request process. In this illustrative example, the vehicle computing system is asked to serve out recorded data to a medical service provider. Although an automatic provision of recently recorded data (such as data that caused an emergency call to be placed) may accompany a 911 call, medical providers may also request data.

For example, if a patient is requested to wear a medical condition tracking device to record a medical condition, the device may report periodically or solely to a vehicle computing system. In this instance, relevant data may be stored only on the vehicle computing system. Either before a visit, or in order to track patient progress or monitor a condition, a medical service provider may wish to receive a copy of the data.

In this illustrative embodiment, a vehicle computing system receives a data request 501, from, for example, a medical service provider. This request may carry with it some form of identification of the provider that automatically provides permission for the request, or at least identifies the provider for the vehicle occupant.

After the request has been received, the system notifies the vehicle occupant of the request 503 (it may also be possible that certain providers with sufficient identification are permitted to automatically access the system, bypassing the manual identification process detailed in this illustrative embodiment).

If the vehicle occupant approves the data request 505, the vehicle computing system may further request that the user input a PIN or a password 507. If included, this may be required for release of data by legal concerns, or it may be a user-enabled option to further protect potentially sensitive data.

If the input PIN/password is incorrect, the system warns the user 509 and then checks to see if too many incorrect passwords have been input (or a timeout has occurred, etc)

511. If the proper identification code is provided 507, the system sends the requested data to the requesting party 513.

What is claimed:

1. A computer-implemented method comprising:
    detecting, via a vehicle computing system (VCS), a monitoring device;
    periodically downloading health information from the monitoring device to the VCS;
    storing downloaded information on the VCS in association with a vehicle occupant;
    receiving a request from a remote medical provider to access stored information;
    notifying the occupant of the request through the vehicle; and
    after receiving occupant's permission through the vehicle, transmitting the stored information to the remote medical provider.

2. The method of claim 1, further including determining that the occupant is associated with a wireless device present in a vehicle, the wireless device corresponding to an occupant for whom a user account for storage of device information was created.

3. The method of claim 2, wherein the wireless device is the monitoring device.

4. The method of claim 1, wherein the monitoring device includes a monitoring device provided as part of a vehicle.

5. The method of claim 4, wherein the monitoring device is a heart rate monitor.

6. The method of claim 5, wherein the heart rate monitor is provided as part of a steering wheel.

7. The method of claim 5, wherein the heart rate monitor is provided as part of a vehicle seat.

8. The method of claim 4, wherein the monitoring device includes a weight sensor.

9. The method of claim 1, further comprising, wirelessly relaying stored downloaded device information to a remote healthcare provider system.

10. The method of claim 2, further comprising:
    accessing a remote user medical profile to download user medical information;
    updating the user account with the downloaded user medical information.

11. The method of claim 10, further comprising:
    wirelessly uploading downloaded device information to the remote user medical profile.

12. The method of claim 2, further comprising:
    uploading downloaded device information to the wireless device.

13. The method of claim 1, wherein the periodically downloading further comprises downloading at least when a signal from the active device indicates that a parameter measured by the monitoring device exceeds a threshold.

14. The method of claim 13, further comprising:
    providing a warning in response the signal from the monitoring device indicating that the parameter measured by the monitoring device exceeds the threshold.

15. The method of claim 14, further comprising providing emergency assistance information when the signal from the monitoring device indicating that the parameter measured by the monitoring device exceeds the threshold.

16. The method of claim 15, wherein the emergency assistance information includes an option to immediately dial an emergency operator through the VCS.

* * * * *